(12) United States Patent
Townsend et al.

(10) Patent No.: US 12,186,161 B2
(45) Date of Patent: *Jan. 7, 2025

(54) DRYPAD WITH RAPID ABSORPTION AND LIQUID REMOVAL

(71) Applicant: Medline Industries, LP, Northfield, IL (US)

(72) Inventors: Caleb Townsend, Davis, IL (US); Vincent Hahn, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,263

(22) Filed: Oct. 24, 2023

(65) Prior Publication Data

US 2024/0058175 A1    Feb. 22, 2024

Related U.S. Application Data

(63) Continuation of application No. 16/166,408, filed on Oct. 22, 2018, now Pat. No. 11,839,528.

(51) Int. Cl.
| | |
|---|---|
| *A61F 13/0203* | (2024.01) |
| *A61F 13/0206* | (2024.01) |
| *A61F 13/15* | (2006.01) |
| *A61F 13/513* | (2006.01) |
| *A61F 13/53* | (2006.01) |
| *B32B 5/02* | (2006.01) |
| *B32B 5/26* | (2006.01) |

(52) U.S. Cl.
CPC ...... *A61F 13/0223* (2013.01); *A61F 13/0209* (2013.01); *A61F 13/15268* (2013.01); *A61F 13/15617* (2013.01); *A61F 13/51305* (2013.01); *A61F 2013/15154* (2013.01); *A61F 2013/530255* (2013.01); *B32B 5/022* (2013.01); *B32B 5/26* (2013.01); *B32B 2262/067* (2013.01); *B32B 2262/14* (2013.01); *B32B 2307/716* (2013.01)

(58) Field of Classification Search
CPC .............. A61F 13/0209; A61F 13/0223; A61F 13/15268; A61F 13/15617; A61F 13/51305; A61F 2013/15154; A61F 13/00029; A61F 5/4401; A61F 5/451; B32B 2262/14; A61M 1/00; A61M 2202/0496

See application file for complete search history.

(56) References Cited

U.S. PATENT DOCUMENTS 4,360,015 A * 11/1982 Mayer ............... A61F 13/00029
602/47
4,747,166 A *  5/1988 Kuntz .................... A61F 5/455
4/144.1

(Continued)

*Primary Examiner* — Michele Kidwell
(74) *Attorney, Agent, or Firm* — Fitch, Even, Tabin & Flannery LLP

(57) ABSTRACT

Disclosed is a liquid removal drypad and liquid removal system suitable for absorbing and removing liquid produced by an individual. The drypad can include one or more perforated conduits arranged with an absorbent material. A source of reduced pressure can be connected to the one or more perforated conduits to remove liquid from the drypad. The drypad can be positioned under a patient and liquid produced by the individual can be removed by applying reduced pressure to the drypad. The drypad can be made by combining one or more conduits with an absorbent material.

20 Claims, 3 Drawing Sheets

(56) References Cited

U.S. PATENT DOCUMENTS

| | | | | |
|---|---|---|---|---|
| 4,870,710 | A * | 10/1989 | Hartmann | A61F 5/48 5/606 |
| 5,911,222 | A * | 6/1999 | Lawrence | A61F 5/455 600/574 |
| 7,220,250 | B2 * | 5/2007 | Suzuki | A61F 5/451 604/317 |
| 8,241,262 | B2 * | 8/2012 | Mahnensmith | A61F 13/15 604/352 |
| 10,159,607 | B2 * | 12/2018 | Monson | G16H 40/20 |
| 10,559,187 | B2 * | 2/2020 | Flanagan | G16H 40/63 |
| 10,716,715 | B2 * | 7/2020 | Severns | G06K 7/10158 |
| 11,839,528 | B2 * | 12/2023 | Townsend | A61F 13/0223 |
| 2003/0195484 | A1 * | 10/2003 | Harvie | A61F 5/453 604/355 |
| 2005/0070862 | A1 * | 3/2005 | Tazoe | A61F 5/4404 604/327 |
| 2006/0015081 | A1 * | 1/2006 | Suzuki | A61F 5/451 604/329 |
| 2007/0035405 | A1 * | 2/2007 | Wada | A61F 13/42 340/604 |
| 2009/0326493 | A1 * | 12/2009 | Wada | G01N 33/493 604/361 |
| 2012/0103347 | A1 * | 5/2012 | Wheaton | A61F 5/453 128/885 |
| 2012/0256750 | A1 * | 10/2012 | Novak | A61F 13/42 340/573.5 |

\* cited by examiner

DRYPAD WITH RAPID ABSORPTION AND LIQUID REMOVAL

CROSS-REFERENCE TO RELATED APPLICATION

This application is a continuation of U.S. application Ser. No. 16/166,408, filed Oct. 22, 2018, the entire contents of which are incorporated herein by reference.

TECHNICAL FIELD

The disclosure relates generally to a drypad with the capability of rapidly absorbing and removing liquid such as urine or other bodily secretions from a patient. In related embodiments the disclosure relates to methods of rapidly absorbing fluid into a drypad, of removing urine or other fluids from a drypad, and methods of making liquid removal drypads.

BACKGROUND

Various types of absorbent underpads and drypads are used to collect urine and other bodily fluids by placement of the underpad or drypad between bedding and a patient. Such devices are used in many healthcare settings such as critical and non-critical nursing units, labor and delivery rooms, and operating rooms.

Several types of urine management devices have been sold commercially. Disposable underpads (also known colloquially as "chucks") are known, these including a layer of a fluid-resistant backing, an absorbent layer, and a fluid-permeable top sheet. Disposable underpads are generally inexpensive but have limited absorbency. Some underpads are launderable and include an absorbent textile sewn or otherwise fixed to a backing for reinforcement.

A relatively recent innovation in the fluid management space has included the development of drypads, also known colloquially as "premium underpads." Drypads generally include multiple layers of different materials to quickly absorb fluids and provide a surface that is dry to the touch. Drypads can include super-absorptive polymers that assist with the absorption of fluids. An exemplary drypad is disclosed in U.S. Pat. No. 8,791,321. Drypads generally are better than underpads in keeping bedridden patients comfortable and sanitary.

Underpad "chucks" and drypads provide insufficient absorbency when large amounts of fluid are deposited onto the absorbent core of the product over a short period of time, such as when a patient voids his or her bladder quickly, or when fluids are emitted during childbirth. It would be desirable to provide a liquid management device that is capable of quickly absorbing and removing a large outflow of urine or other liquid deposited on the drypad. Such a device would avoid saturation of bedding, protection of floors, and maintain sanitary surfaces.

It has now been discovered that a drypad can be constructed to rapidly absorb and remove large quantities of liquid expelled from an individual under which the drypad is disposed. Generally, the drypad can include a structure comprising an absorbent material arranged with one or more perforated conduits capable of creating an area of suction on the topmost layer of the drypad and transporting liquid away from the drypad when subject to reduced pressure. A drypad can optionally include a hydrophobic layer to attenuate penetration of liquid from the drypad. The drypad can be connected to a suction device to remove urine or other liquid therefrom to form a liquid containment system. The system can optionally include a controller capable of activating the source of reduced pressure upon occurrence of an event or condition.

The system can be used in connection with a method of quickly absorbing and removing liquid from a drypad. Generally, the method includes disposing a drypad under an individual, allowing the individual to emit urine or other fluids onto the drypad, and applying reduced pressure to one or more conduits provided in the drypad to remove liquid from the drypad. A method of forming a liquid removal drypad includes forming a structure including one or more perforated conduits arranged with an absorbent material and attaching a hydrophobic layer to the structure. Edges of the absorbent material and an optional hydrophobic layer can be sealed while retaining a port accessing the one or more conduits on an exterior of the drypad.

As described in more detail below, the disclosed drypad and liquid removal system are capable of rapidly absorbing and facilitating removal of liquid emitted by a bedridden patient. The drypad can address prior problems of conventional drypads being unable to quickly absorb or otherwise accommodate large quantities of liquid deposited over a short period of time.

BRIEF DESCRIPTION OF THE DRAWINGS

FIG. 6A is a side elevation and FIGS. 6B-D are cross-sectional views.

DETAILED DESCRIPTION

Figure 1:
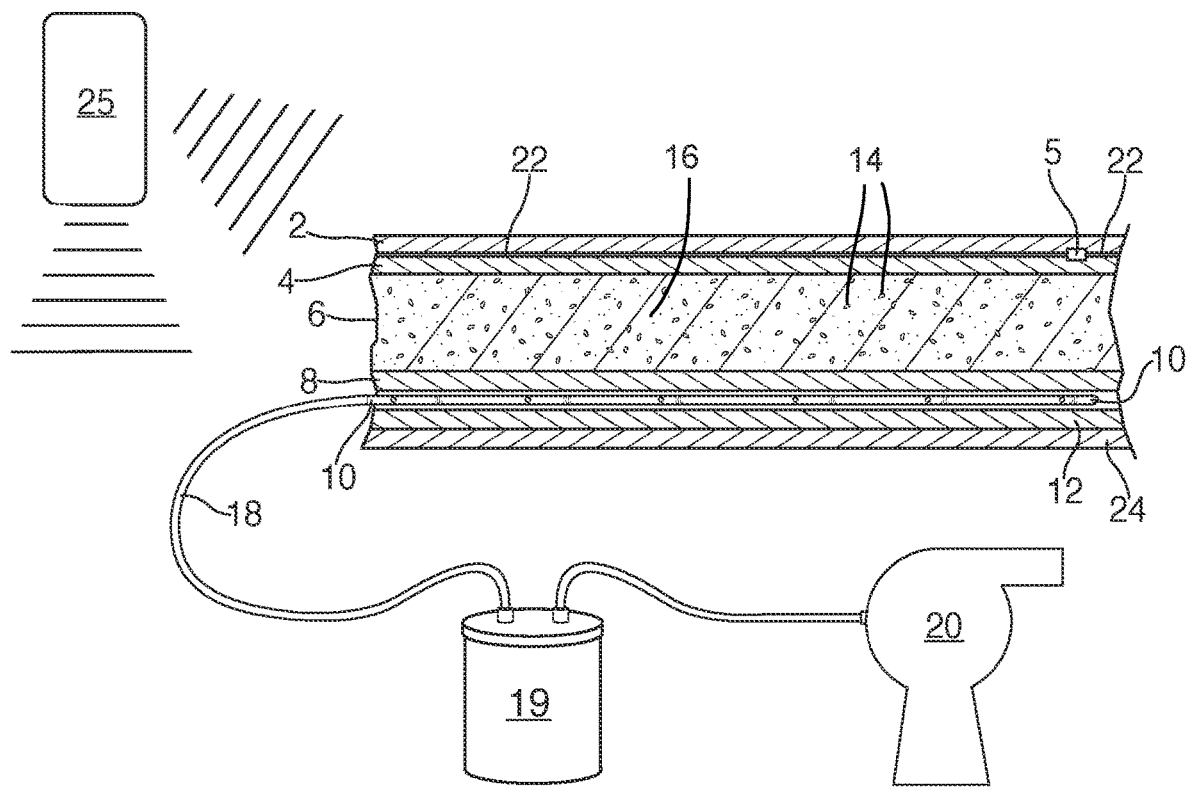
FIGS. 1, 3, 4, and 5 each illustrate different embodiments of a rapid liquid absorption and removal system in representational form and illustrating different disposable removal drypads in cross section.

A drypad generally may be constructed in accordance with the teachings of U.S. Pat. No. 8,791,321, except that the drypad will include one or more liquid transport conduits and a port for connection to a source of suction. The drypad generally otherwise comprises plural layers of different functional materials as described below. When connected to a source of suction, a liquid rapid absorption and removal system is formed. The system may include a canister or other device for collecting liquid for subsequent disposal or laboratory analysis. The drypad may be made as a disposable, single use device in some embodiments, or may be made as a reusable, launderable drypad in other embodiments.

A conduit can transport liquid away from a drypad when the conduit is subjected to reduced pressure. The conduit can generally be constructed of any material, e.g. natural or synthetic polymers, metal, etc. Conduits can generally have any hollow cross-section, e.g., circular, elliptical, rectangular, etc., useful for transporting fluids. The conduit can generally be positioned at any location in an absorbent material or relative to a position of absorbent material. One or more perforations can be provided through a wall of a conduit to provide an aperture through which liquid can be drawn when an interior of the conduit is subject to reduced pressure. One or more perforations can be formed at any one or more of an end of a conduit, or at various points along a length of the conduit. In some embodiments, perforations comprise pores in a porous material of which a conduit is constructed.

A drypad can include one or more conduits formed in any structure, such as one or more of straight conduits, curved conduits, coiled conduits, grid-shaped conduits, an array of conduits, a network of conduits, etc., or any combination thereof. In some embodiments more than one conduit can be arranged in parallel or in series in a drypad. A drypad including multiple conduits can be constructed such that the multiple conduits are interconnected to transport liquid to a single point on an exterior of the drypad. Alternatively, multiple conduits can be separate and not interconnected and transport liquid to separate points on an exterior of the drypad. Any combination or modifications of such constructions are contemplated. Generally, one or more conduits can be connected to one or more ports on an exterior surface of a drypad.

Any one or more suitable sources of reduced pressure such as pumps, vacuums, motors, a hospital or clinic central suction system, etc. can be connected to one or more conduits to remove liquid from a drypad. A source of reduced pressure can be connected to a port on an exterior of a drypad to apply reduced pressure to an interior of a conduit. Any type of connector such as a line, hose, etc. can be use used to provide a connection between a source of reduced pressure and a port. A connector can generally be constructed of any material such as a polymer, a metal, etc.

A source of reduced pressure can be manually or automatically controlled as needed to remove liquids from a drypad. A manual control device can comprise a switch activatable by a patient or caregiver such as a nurse or nurse assistant to activate a source of reduced pressure. Such switch can activate a source of reduced pressure or actuate a valve between an active source of reduced pressure and a conduit. Manual control can also comprise merely attaching a connector between a source of reduced pressure and a port on a drypad. The suction may be applied as indefinite suction, i.e., continuous suction through a predefined period of use of the drypad. Alternatively, an automatic control can comprise any type of controller programmed to activate and deactivate a source of reduced pressure or programmed to actuate a valve between an active source of reduced pressure and a conduit. Such controller can trigger initiation of suction based on any desired condition, event, or schedule. In some embodiments the suction is applied intermittently at predetermined intervals and for a predetermined amount of time per interval (e.g. for two minutes in each fifteen minute interval).

The controller can generally include any configuration such as electronic, mechanical, computerized, programmable, etc. for controlling application of reduced pressure to a conduit. The controller may intermittently activate application of reduced pressure to a conduit based on a predetermined schedule or upon receiving a signal indicating a need for reduced pressure, and can maintain application of reduced pressure to a conduit indefinitely, for a predetermined time, until receiving a signal indicating that reduced pressure should be stopped, etc. The controller can be operably connected to a source of reduced pressure, a drypad, a sensor, a switch, etc. in any manner such as by wiring, wirelessly, mechanically, etc. For example, the controller may be programmed to activate suction when a sensor is triggered and to leave the suction activated for a predetermined period (e.g. two minutes).

In exemplary embodiments, a drypad can include a conductor in the form of an open circuit. Urine and many other bodily fluids are generally electrically conductive, and when liquid contacts the conductor, conduction of electricity through the liquid can close an electrical circuit. A controller connected to such a circuit can activate application of reduced pressure to a conduit upon the wetting of the circuit. A conductor, e.g. wire, foil, conductive ink, etc., can be formed on or in any part of a drypad. Any useful open circuit pattern such as an incomplete loop, broken grid, serpentine pattern, etc. can be used to form a conductor.

A drypad can generally include any one or more types of absorbent material. In some aspects, absorbent materials can include any one or more of properties of facilitating drawing-in of liquid, passage of liquid, absorption of liquid, retention of liquid, etc. Absorbent materials can be natural, synthetic, and any combination thereof. Absorbent materials can be in the form of fibers, foam, fluff, pulp, beads, woven fabrics, nonwoven fabrics, etc., or any combinations thereof. In exemplary embodiments, absorbent materials can be provided in one or more layers. Each layer can include a single material, a homogenous mixture of materials, a non-homogenous mixture of materials, etc., or any combinations thereof.

Any suitable natural fiber can be included in an absorbent material. Exemplary natural fibers include those comprising cellulose such as plant fibers, field crop fibers, wood fibers, wood-pulp fluff, macerated wood pulp, fluff pulp fibers, tissue, cotton, etc., or any combinations thereof. Exemplary synthetic fibers include polymers such as polyethylene, polyethylene terephthalate, polypropylene, polyamide, rayon, nylon, etc., or any combinations thereof.

Fibers can be treated to provide hydrophilic characteristics for fluid permeability and absorption. Exemplary treatments include coating a surface of a material with a hydrophilic surfactant, surface treatments such as corona and plasma treatment, applying a hydrophilic coating by a plasma polymerization process, contacting fibers with a solution of hydrophilic monomers and radical polymerization initiators and exposing the fibers to UV radiation, etc., or any combinations thereof.

An absorbent material can also include an absorbent polymer such as a super-absorbent polymer. Exemplary super-absorbent polymers include, for example, polymers and copolymers of acrylic acid, methacrylic acid and salts thereof (including alkali metal salts such as sodium salts, or alkaline earth salts thereof), polyacrylamide polymers and copolymers, ethylene maleic anhydride copolymers, cross-linked carboxy-methyl-celluloses, polyacrylate/polyacrylamide copolymers, polyvinyl alcohol copolymers, cross-linked polyethylene oxides, starch grafted copolymers of polyacrylonitrile, etc. The super-absorbent polymers can also be cross-linked to a suitable degree. Exemplary absorbent materials include a layer comprising cellulose fluff, such as wood pulp fluff, and an absorbent polymer.

Exemplary nonwoven materials include staple nonwoven materials, meltblown nonwoven materials, spunmelt nonwoven materials, spunbond nonwoven materials, spunbond meltblown spunbond (SMS) materials, spun lace materials, needle-felted materials, thermal-bonded nonwoven materials, trough-air-bonded nonwoven material, spunlaid nonwoven material, air-laid nonwoven materials, etc., or any combinations thereof. Exemplary woven materials include generally any type of fiber, thread, yarn, etc. woven in a plain, twilled, plain dutch, twilled dutch, satin, basketweave, jacquard, dobby, leno, quilted, etc. pattern.

The drypad should include a hydrophobic layer to attenuate penetration of a liquid from the drypad to a surface such as a bed. A hydrophobic layer can be optionally gas permeable to provide air circulation within and through the drypad, while also attenuating penetration of liquids. The gas permeability of a hydrophobic film can be achieved any known method such as providing woven or nonwoven fibers treated hydrophobic materials, providing polymeric sheets having perforations sized to prevent flow of liquid and allow gas transfer, etc. Exemplary materials for a hydrophobic layer include polyethylene, polypropylene, poly(lactic acid), polyhydroxybutyrate, tapioca starch, starch-based biodegradable material, polyamide, rayon, nylon, copolymers thereof, etc., or any combinations thereof. The hydrophobic film can be provided as a base layer for contacting a substrate such as bedding. In other aspects, a base layer of a woven or nonwoven material of absorbent or nonabsorbent nature may be placed against or otherwise attached to a hydrophobic layer to prevent slippage of a drypad against a surface such as bedding. Exemplary drypads can include a hydrophobic layer adjacent to a structure comprising one or more layers of absorbent material arranged with one or more perforated conduits.

FIG. 1 illustrates a cross-section view of an embodiment of a drypad that rapidly absorbs and removes liquid including a first layer 4, a second layer 6, and a third layer 8, with the second layer between the first and third layers. The first and third layers comprise tissue and the second layer comprises wood fluff 16 and super-absorbent polymer beads 14. One or more perforated conduits 10 are arranged between the third layer 8 and a hydrophobic layer 12 constructed of a polypropylene film. A liquid-permeable nonwoven layer 2 is provided as a top sheet. The hydrophobic layer 12 is provided between a nonwoven base layer 24 and the one or more conduits 10. An open circuit 22 of conductive ink is printed on the nonwoven layer 2 and is disposed between the nonwoven layer 2 and the first layer 4. In other embodiments the circuit could be printed on the hydrophobic layer 12 or on any other suitable layer. The conductive ink is optional and it is contemplated that the ink might be omitted. The conduits may be composed of any suitable material, for example, perforated medical tubing. The nonwoven base layer may comprise a higher-friction material than the hydrophobic layer to inhibit slippage.

The embodiment of the urine removal system illustrated in FIG. 1 includes a wireless controller 25 capable of communicating with a vacuum pump 20 and a wireless communicator 5 embedded in the drypad. The communicator 5 is connected to the circuit 22. A hose 18 connects the one or more conduits 10 to the fluid canister 19 and vacuum pump 20. When sufficient urine is deposited on the drypad to close the circuit 22, the wireless communicator 5 connected to the circuit sends a signal to the controller 25. The controller then sends a signal to the pump 20 to apply reduced pressure to the conduits and begin removal of liquid. It is contemplated that the controller may initiate suction via other vacuum sources, such as house suction. The controller is programmed to deactivate the pump 20 after an elapsed time passes from the activation of the pump.

Figure 2:
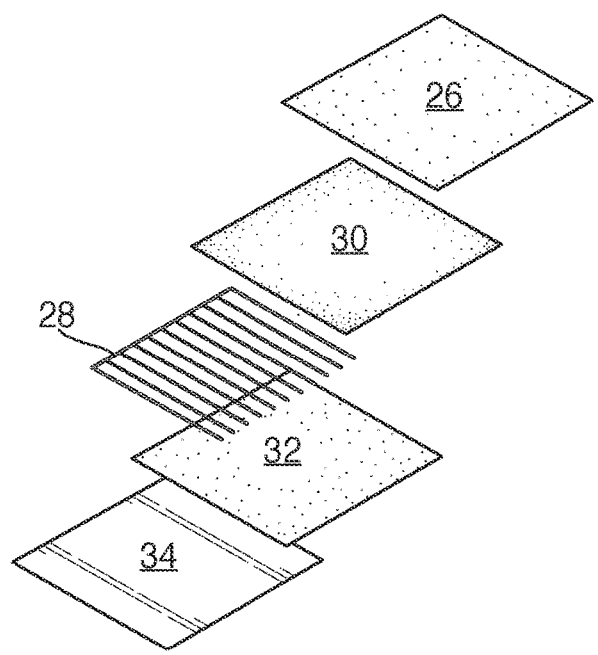
FIG. 2 is exploded view of an embodiment of a reusable liquid rapid absorption and removal drypad.

FIG. 2 illustrates a cross-section view of another embodiment of a urine removal drypad. A group of conduits 28 constructed in parallel is disposed adjacent padding layer 30 which is disposed beneath an absorbent acquiring layer 26. The drypad further includes a hydrophobic backing layer 34 and a soaking layer 32, the soaking layer including an absorbent material.

Figure 3:
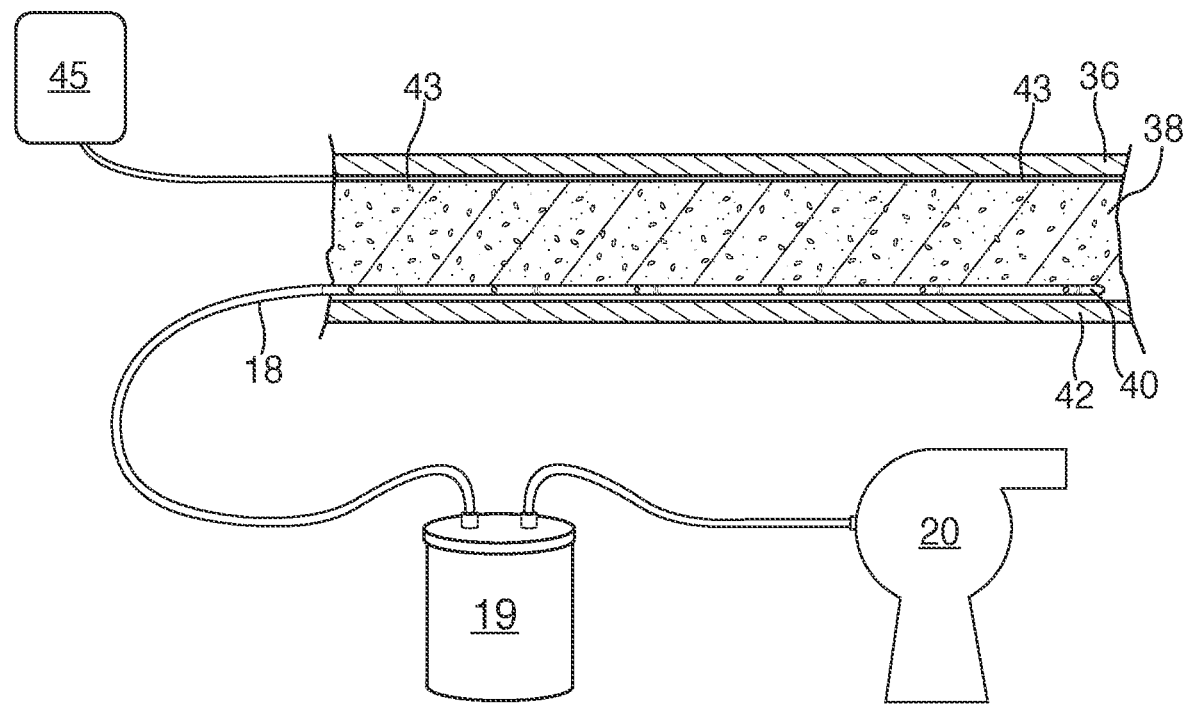

FIG. 3 illustrates yet another cross-section view of embodiment of a urine removal drypad. An absorbent layer 38 is disposed between a liquid-permeable nonwoven layer 36 and a hydrophobic layer 42. A perforated conduit 40 is provided between the absorbent layer and the hydrophobic layer. An open circuit formed of metal foil 43 is disposed between the nonwoven layer 36 and the absorbent layer 38. Again, the metal foil is optional and the drypad could be prepared without the use of the foil. The urine removal system illustrated in FIG. 3 includes the drypad, a controller 45 wired to both the open circuit and a vacuum pump 20 and canister 19. The pump is connected to the conduit by a hose 18. When sufficient urine is deposited on the drypad to close the circuit 43, the controller 45 sends a signal to the pump 20 to apply reduced pressure to the conduit and begin removal of liquid. When enough liquid has been removed or absorbed by the drypad for the circuit to be opened, the controller stops the pump.

Figure 4:
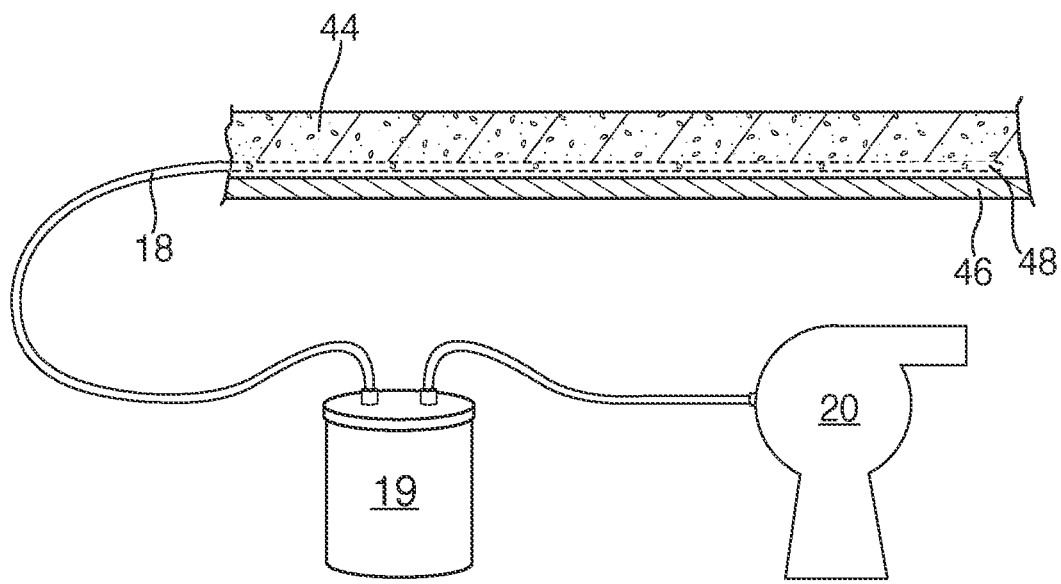

FIG. 4 provides a cross-sectional view of another embodiment of a urine removal drypad. A perforated conduit 48 is disposed in a layer of absorbent material 44. A hydrophobic layer 46 is provided on a surface of the layer of absorbent material. The urine removal system illustrated in FIG. 4 includes a canister 19 and vacuum pump 20 connected to the conduit 48 of the drypad by a tube 18. A user can activate the pump when urine needs to be removed from the drypad or indefinite suction may be employed. The drypad can be laundered and reused.

Figure 5:
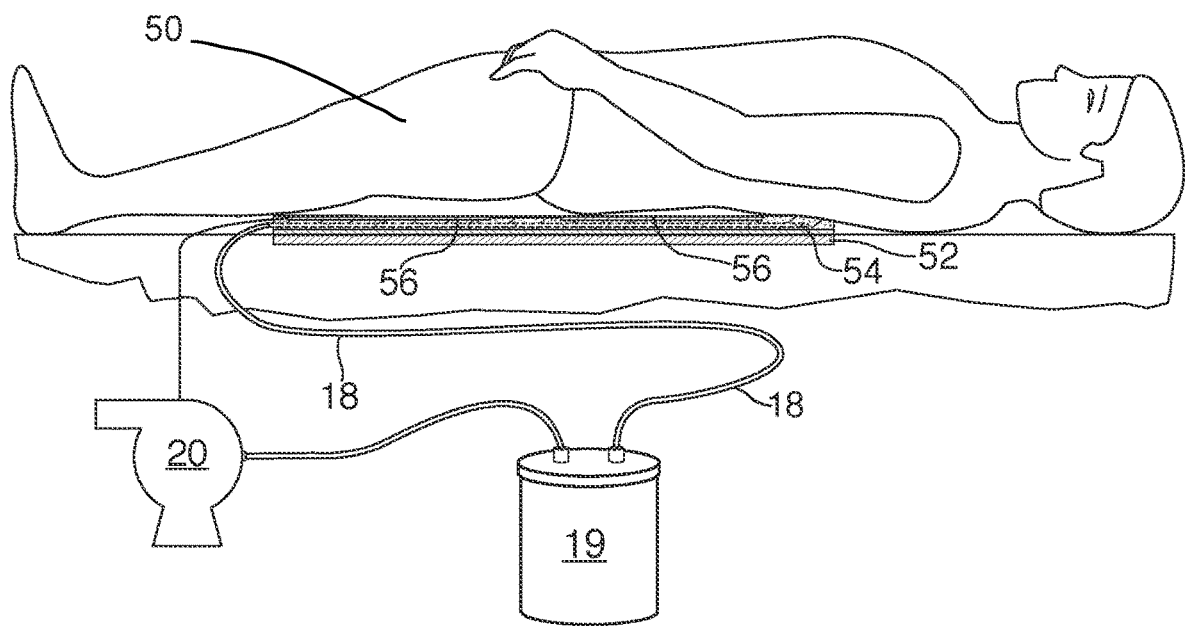

A method of removing liquid from a drypad can generally include any manner of disposing a drypad including one or more perforated conduits arranged with an absorbent material under a subject, e.g. a patient. The subject is allowed to urinate onto the drypad and reduced pressure is applied to the one or perforated conduits to remove at least a portion of the liquid from the drypad. FIG. 5 illustrates a patient 50 positioned over an embodiment of a urine removal drypad including a perforated conduit 54 disposed in an absorbent material 52. The illustrated patient is a non-ambulatory patient for which the drypad is used for urine management, but it is also contemplated that the patient could be a different patient, such as a pregnant woman in childbirth. An open circuit 56 of conductive ink is printed on the absorbent material. The urine removal system illustrated in FIG. 5 includes the drypad and a vacuum pump 20 and canister 19. The conduit 54 is connected to the pump and canister 20 by a hose 18 and the circuit 56 is wired to the pump. When sufficient urine is deposited on the drypad to contact the separate portions of the circuit 56 and thereby close the circuit, the pump 20 applies reduced pressure to the conduit to begin removal of liquid. The pump includes a controller that automatically stops the pump after a predetermined period of operation.

A drypad as described herein can be assembled by any suitable method. Generally, one or more conduits can be arranged with an absorbent material in any manner such as disposing one or more conduits on an absorbent material, layering of absorbent material with one or more conduits, interspersing of one or more conduits within absorbent material, insertion of one or more conduits into absorbent material, etc., or any combinations thereof. A hydrophobic layer can be provided on a structure including one or more conduits and absorbent material. Sheets of absorbent and hydrophobic materials can be drawn from rolls and combined in a desired order. The edges of absorbent and hydrophobic materials can be sealed or otherwise adhered together with one or more conduits within the stack, while ensuring that a port to the one or more conduits is accessible on an exterior of surface of a drypad. Layers of absorbent and hydrophobic materials can be cut to appropriate size before or after combining with the one or more conduits.

Figure 6A:
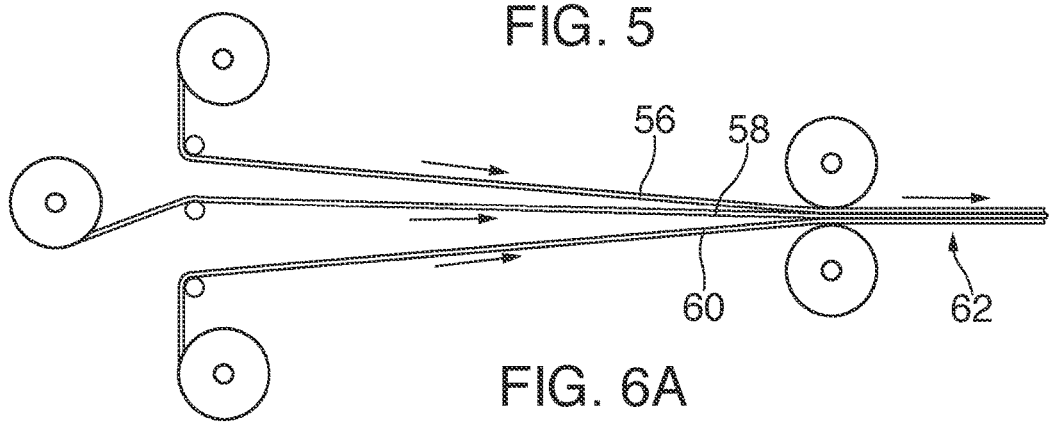
FIGS. 6A-6D illustrate various steps in an exemplary method of making a drypad.

FIGS. 6A through 6D illustrate an exemplary embodiment of a method of making a drypad. FIG. 6A illustrates a nonwoven layer 56 of absorbent material, a layer 58 including cellulose fluff and super-absorbent polymer, and a layer

Figure 6B:
Figure 6C:
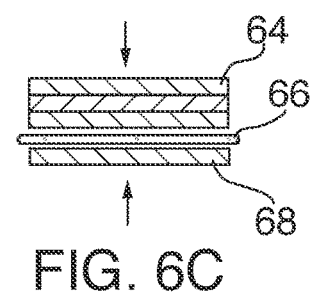
Figure 6D:
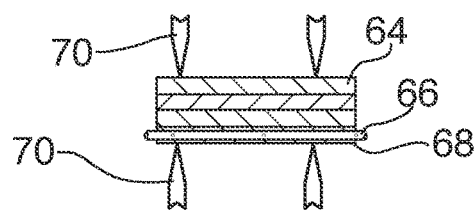

60 of tissue being drawn from rolls and combined into a drawn layering 62. FIG. 6B illustrates the drawn layering 62 being severed into a cut layering 64. FIG. 6C illustrates the formation of a stack of a hydrophobic layer 68 with a structure including the cut layering 64 and a perforated conduit 66. FIG. 6D illustrates edges of the stack being sealed together via sealing apparatus 70 to form a drypad while retaining a port accessing the conduit on an exterior surface of the drypad.

It is thus seen that a drypad rapid absorption and urine removal system are provided in accordance with the foregoing teachings. When constructed in accordance with the present teachings, a liquid removal drypad can have several desirable attributes. Particularly useful features include the drypad's ability to absorb liquids quickly, contain fluid within the absorbent core, and facilitate removal liquids from the drypad. Although the drypads describe herein are useful for urine removal, more generally the drypad may be used to absorb and remove any bodily fluid, e.g. water, urine, blood, amniotic fluid, diarrhea, etc. Generally, the drypad and system described herein can be used in any facility or setting, e.g. medical, nursing, veterinary, assisted-living, home, vehicle, etc. The drypad can be made to be disposable or reusable.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A liquid removal drypad comprising:
    a structure comprising one or more layers of absorbent material arranged with one or more perforated conduits, the one or more perforated conduits being capable transporting liquid away from the drypad when subject to reduced pressure;
    a liquid-permeable nonwoven layer disposed on a first side of the structure, an open electrical circuit comprising conductive ink printed on the liquid-permeable nonwoven layer, the open electrical circuit capable of being closed by conduction of electricity through a body of liquid contacting separate portions of the circuit; and
    a hydrophobic layer disposed on a second side of the structure.

2. The liquid removal drypad of claim 1, the one or more layers of absorbent material comprising a first layer, a second layer, and a third layer, the second layer being disposed between the first layer and the third layer, and the one or more perforated conduits being disposed between the third layer and the hydrophobic layer.

3. The liquid removal drypad of claim 2, the first and third layers comprising tissue, the second layer comprising cellulose fluff and an absorbent polymer, the hydrophobic layer comprising a polypropylene film.

4. The liquid removal drypad of claim 1, further comprising a nonwoven base layer, the hydrophobic layer being disposed between the one or more perforated conduits and the nonwoven base layer.

5. The liquid removal drypad of claim 1, the one or more layers of absorbent material comprising an absorbent sheet, a padding layer, and a soaking layer, the one or more perforated conduits being disposed between the padding layer and the soaking layer, and the soaking layer being disposed between the hydrophobic layer and the padding layer.

6. The liquid removal drypad of claim 5, the padding layer comprising cellulose fluff and the soaking layer comprising an absorbent material.

7. The liquid removal drypad of claim 1, the one or more layers of absorbent material comprising an absorbent layer, the absorbent layer being disposed between the liquid-permeable nonwoven layer and the hydrophobic layer, the one or more perforated conduits being arranged between the liquid-permeable nonwoven layer and the absorbent layer or between the absorbent layer and the hydrophobic layer.

8. The liquid removal drypad of claim 1 being reusable after laundering.

9. The liquid removal drypad of claim 1, the open electrical circuit being printed on a surface of the liquid-permeable nonwoven layer facing the one or more layers of absorbent material.

10. A liquid removal system comprising:
    the liquid removal drypad according to claim 1,
    a source of reduced pressure connected to the one or more perforated conduits; and
    a controller programmed to activate the source of reduced pressure upon closure of the circuit.

11. The liquid removal system of claim 10, the controller being programmed to deactivate the source of reduced pressure after the activation of the source of reduced pressure.

12. The liquid removal system of claim 10, the controller being programmed to deactivate the source of reduced pressure based on an elapsed time from the activation of the source of reduced pressure.

13. A method of removing liquid from a drypad, the method comprising:
    disposing the drypad under a patient, the drypad comprising:
        a structure comprising one or more layers of absorbent material arranged with one or more perforated conduits, the one or more perforated conduits being capable transporting liquid away from the drypad when subject to reduced pressure,
        a liquid-permeable nonwoven layer disposed on a first side of the structure, an open electrical circuit comprising conductive ink printed on the liquid-permeable nonwoven layer, the open electrical circuit capable of being closed by conduction of electricity through a body of liquid contacting separate portions of the circuit, and a hydrophobic layer disposed on a second side of the structure;

allowing the patient to excrete bodily fluid on the drypad;

applying reduced pressure to the one or more perforated conduits to remove at least a portion of the fluid from the drypad.

14. The method of claim 13, the method further comprising allowing the liquid to contact separate portions of the circuit and close to the circuit to activate the source of the reduced pressure.

15. The method of claim 13, the bodily fluid comprising urine.

16. A method of making a liquid removal drypad, the method comprising:

forming a stack of a structure and a hydrophobic layer, the structure including one or more layers of absorbent material and one or more perforated conduits, and the hydrophobic layer including an open electrical circuit comprising conductive ink printed thereon; and sealing edges of the one or more layers of absorbent material and the hydrophobic layer while retaining a port accessing the one or more perforated conduits on an exterior of the drypad.

17. The method of claim 16, the one or more perforated conduits being between the one or more layers of absorbent material and the hydrophobic layer.

18. The method of claim 16, the one or more layers of absorbent material include a nonwoven layer, a layer including cellulose fluff and a super-absorbent polymer, and a layer of tissue.

19. The method of claim 18, the method further comprising drawing the nonwoven layer, the layer including cellulose fluff and a super-absorbent polymer, and the layer including tissue from respective rolls to form a drawn layering.

20. The method of claim 19, the method further comprising severing the drawn layering to form a cut layering, and then stacking the cut layering with the one or more perforated conduits and the hydrophobic layer to form the stack.

* * * * *